United States Patent [19]

Hayman et al.

[11] Patent Number: 5,183,455
[45] Date of Patent: * Feb. 2, 1993

[54] APPARATUS FOR IN SITU RADIOTHERAPY

[75] Inventors: Michael H. Hayman; Lee R. Morgan, both of New Orleans; Samuel F. Liprie, Lake Charles, all of La.

[73] Assignee: Omnitron International, Inc., Houston, Tex.

[*] Notice: The portion of the term of this patent subsequent to Dec. 11, 2007 has been disclaimed.

[21] Appl. No.: 609,437

[22] Filed: Nov. 5, 1990

Related U.S. Application Data

[63] Continuation-in-part of Ser. No. 255,045, Oct. 7, 1988, Pat. No. 4,976,680.

[51] Int. Cl.⁵ .............................................. A61M 36/04
[52] U.S. Cl. ...................................................... 600/7
[58] Field of Search ........................................ 600/1-8, 600/32

[56] References Cited

U.S. PATENT DOCUMENTS

| | | | |
|---|---|---|---|
| 1,406,509 | 2/1922 | Viol | 600/7 |
| 1,442,051 | 1/1923 | Cummings | 600/8 |
| 1,565,490 | 12/1925 | Muguet | 600/8 |
| 1,603,767 | 10/1926 | Harris | 600/3 |
| 1,954,868 | 4/1934 | Failla et al. | 600/8 |
| 3,750,653 | 8/1973 | Simon | 600/7 |
| 4,240,421 | 12/1980 | Carr | 600/5 |
| 4,588,395 | 5/1986 | Lemelson | 600/7 |
| 4,819,618 | 4/1989 | Liprie | 600/7 |
| 4,861,520 | 8/1989 | Hooft et al. | 600/7 |
| 4,976,680 | 12/1990 | Hayman et al. | 600/7 |

OTHER PUBLICATIONS

Haybittle et al., "British Journal of Radiology", vol. 48, No. 568, Apr. 1975, pp. 295-298.

Primary Examiner—William E. Kamm
Attorney, Agent, or Firm—Fitch, Even, Tabin & Flannery

[57] ABSTRACT

Apparatus for in situ radiotherapy has a flexible catheter having a proximal end for receiving a radioisotope and a distal end for positioning the flexible catheter within a patient to be treated. An anchor, which is permanently connectable to tissues deep inside the patient, has a sealing collar connected to it which seals the distal end of the catheter. The catheter also includes a plug near the distal end which seals the distal end in addititon to the seal provided by the sealing collar. The anchor has a penetration point connected to it to assist a surgeon in implanting the catheter within a tumor. A threaded fastener on the anchor is screwed into the catheter. The flexible catheter can be released remotely from the anchor by unscrewing it. A suture eye is connected to the anchor. The suture eye may be sutured to healthy tissue within the patient when the apparatus is implanted to secure the anchor to the patient. When the radioisotope is not being received, the proximal end of the catheter is sealed by a cylindrical plug connected to a manipulation handle.

14 Claims, 3 Drawing Sheets

APPARATUS FOR IN SITU RADIOTHERAPY

CROSS-REFERENCES TO RELATED APPLICATIONS

This application is a continuation-in-part of application Ser. No. 255,045, filed Oct. 7, 1988 by Hayman, et. al., for Apparatus for In-Situ Radiotherapy, now U.S. Pat. No. 4,976,680.

The following applications are incorporated herein by reference:

Apparatus and Method for the Remote Handling of Highly Radioactive Sources in the Treatment of Cancer, U.S. Ser. No. 255,044, filed Oct. 7, 1988 et. al., now U.S. Pat. No. 4,976,680, issued Dec. 11, 1990.

Ulta-Thin High Dose Iridium Source for Remote Afterloader, U.S. Ser. No. 228,400, filed Aug. 4, 1988 by Liprie, now U.S. Pat. No. 5,084,802.

BACKGROUND OF THE INVENTION

The invention relates generally to an apparatus for in situ radiotherapy of a patient with a radioisotope and more particularly to a guide tube apparatus wherein the tube has a sealing arrangement and a releasable anchor.

It has been found that certain malignancies which are inoperable or non-respectable may advantageously be treated through radiotherapy techniques wherein radioactive objects or pellets are implanted within or in the vicinity of a tumor mass or in some cases at a site from which a tumor has been removed and for which there is concern that malignant cells may have spread. One of the drawbacks which health care professionals have found with such a treatment modality relates to the fact that in order that they may be left within the patient, the radioisotopes, of necessity, must be relatively low intensity emitters. Another drawback is that such radioactive sources must not only be surgically implanted within the patient but also be extracted surgically.

In an improved version of this technique as described in the aforementioned copending applications localized radioactive sources are positioned in proximity to tumor bodies and the like for brief, precise time intervals. Typically a guide tube, such as a hollow needle, a catheter or a lumen is implanted within a tumor mass and exits through the skin of the patient. A source wire having a radioisotope positioned therein is fed into the guide tube and brought into proximity to the tumor mass. Typically the radioactive portion of the wire is composed of an iridium 192 element about 5 millimeters in length which provides highly localized intense gamma radiation to a relatively small volume of tissue. By positioning a number of such guide tubes within a tumor mass and adjusting the longitudinal positions of the radioactive sources within the guide tubes or catheters the entire tumor mass can be exposed to high intensity radiation for a short period of time with little damage to surrounding tissue.

In order to carry out this type of treatment it is, of course, necessary that the radioactive portions of the wires be precisely positioned in relation to the tumors, and ideally no healthy tissue outside the tumor should be exposed to radiation. As a result, errors in the placement of the radioisotopes within the guide tubes are to be avoided.

One of the prior art methods which has been found to provide the requisite precise positioning employs catheters extending into the patient's body, into a portion of the patient's anatomy which is to be treated and then out of the body at points where the catheters are closed and anchored. In the prior art treatment systems typically there are multiple punctures extending into the body, through the organ to be treated and out of body on the other side where anchoring devices hold the exposed catheter ends. The guide tubes extending through the punctures are typically anchored at both ends causing them to be fixed with respect to the tumor. As a result, once it is known how far the various portions of the tumor are located from the entry points of the guide tubes, the relationship between the catheters, and the tumor will not change while the catheters remain in the patient. The use of this system, however, suffers from the drawback that multiple openings are made in the patient's body. Each of the openings is a potential site for entry of infectious agents and will remain open for several days while the radioisotope treatment is carried out.

In other instances where tumors of the prostate, bowel and the like are to be treated, there is no convenient way of anchoring the proximal ends of the catheters, which typically extend slightly past the tumor site. As a result, due to the patient's moving, the guide tubes may slide out of the patient, and at the very least the extent to which the guide tubes extend into and out of the tumor mass would have to be recalibrated each time the radioisotopes are replaced in the guide tubes for treatment.

SUMMARY OF THE INVENTION

An apparatus for in situ radiotherapy is disclosed herein and includes a plurality of flexible catheters. Each of the flexible catheters has a proximal end and a distal end. The distal end, which is adapted to be inserted within the patient, is sealed and has an anchor connected thereto that is connectable in a permanent fashion to tissues of the patient for implantation therein. The anchor is releasably connected to its respective catheter by a screw thread connection. Although the threaded connection effectively seals the distal end of the catheter while the catheter is secured in place, a principal aspect of the present invention is that the catheter be removable leaving the anchor in place in the patient. To assure sealing of the distal end upon such removal, a second seal is placed in each catheter near the anchor. A tubular bushing having a Dacron cuff surrounding it receives each of the flexible catheters and provides an exit point for the flexible catheters when installed in the patient's body.

It is a principal aspect of the present invention to provide an apparatus for in situ radiotherapy which may be implantable deep within a patient's abdominal cavity or other portions of his or her body.

It is another aspect of the present invention to provide an apparatus for in situ radiotherapy having an anchor connected to each of catheters which may be anchored deep within a patient during a surgical procedure.

It is another aspect of the present invention to provide an apparatus for in situ radiotherapy having anchors permanently implanted within the patient but releasably attached to respective catheters so that following the completion of the radiotherapy the anchors may be left within the patient while the catheters may be removed without the necessity of laparascopy or major surgical procedure.

It is another aspect of the present invention to provide an apparatus which removably seals the proximal ends of the catheters left outside the patient's body from contamination when the source wire is not being inserted into the catheters.

It is another aspect of the present invention to provide second sealing apparatus near the distal end of the catheter to further protect against contamination entering the body, particularly when the anchors and their integral first sealing apparatus have been released for removal of the catheters.

Other aspects of the present invention will become obvious to one skilled in the art upon a perusal of this specification and claims in light of the accompanying drawings.

DESCRIPTION OF THE PREFERRED EMBODIMENT

Figure 1:
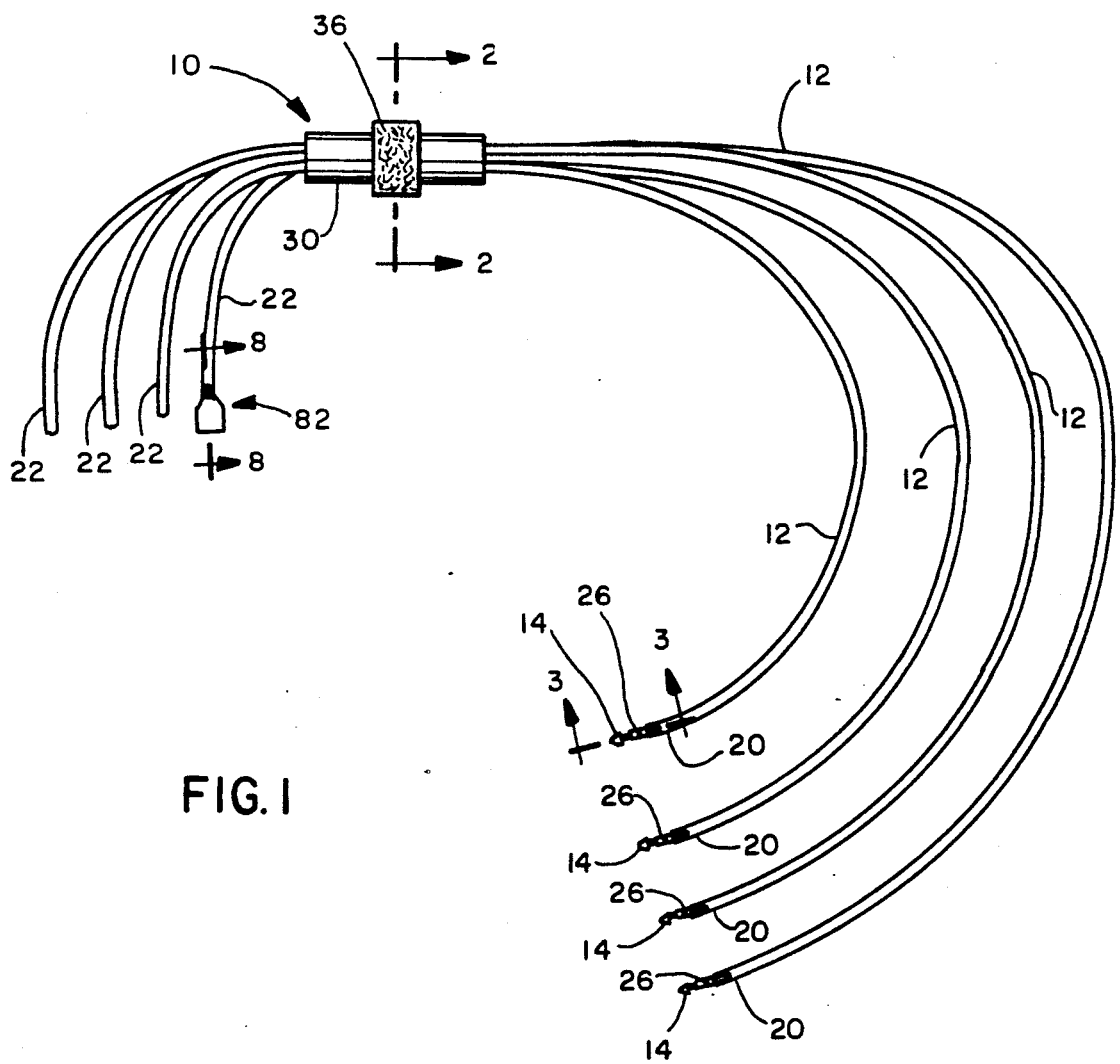
FIG. 1 is an elevational view of an apparatus for in situ radiotherapy embodying the present invention.

Referring now to the drawings and especially to FIG. 1, an apparatus embodying the present invention and generally identified by reference numeral 10 is shown therein. The apparatus 10 has a plurality of flexible guide tubes, catheters of lumens 12. Each of the flexible catheters 12 is composed of a resilient plastic, such as polytetrafluoroethylene, and has a stainless steel anchor 14 removably connected thereto.

A sealing means 18 if formed integrally with each of the anchors 14. The anchors 14 and sealing means 18 are disposed in the respective distal ends 20 of the respective flexible catheters 12. The distal ends 20 are to be disposed within the patient. The proximal end 22 of each of the flexible catheters 12 is adapted to receive a radioistope as will be set forth in detail later. An anchor connector means 24 for releasably connecting each of the anchors 14 to its respective catheter 12 is connected to each of the respective anchors 14. In addition, each of the anchors 14 has connected thereto a patient connection means 26 for connecting the anchors 14 permanently or semi-permanently to tissue deep within the patient.

Figure 2:
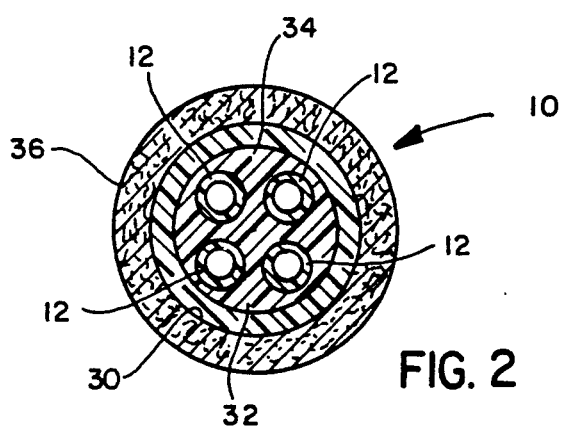
FIG. 2 is a section taken substantially along line 2—2 of FIG. 1 showing details of a bushing through which a plurality of catheters extends.
Figure 5:
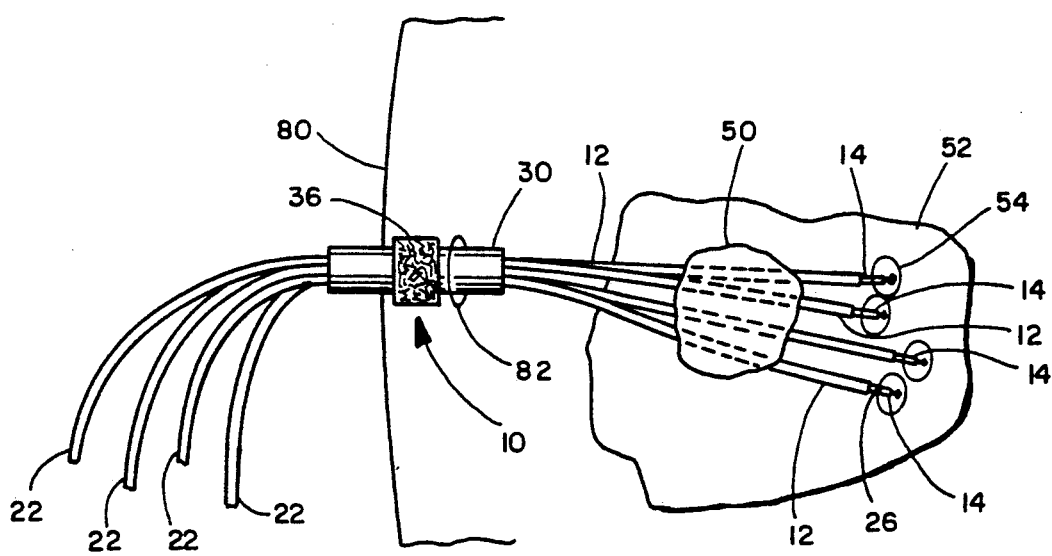
FIG. 5 is a view, partially in section, of the apparatus of FIG. 1 implanted within a patient to be treated by in situ radiotherapy.

The multiple flexible catheters 12 are received by a Silastic tubular common bushing 30, as may best be seen in FIGS. 1, 2, and 5. The bushing 30, in addition to receiving the catheters 12 has an interior portion 32 filled with silicone 34 effectively to seal the inside of the bushing 30. However, the flexible catheters 12 are somewhat free to be slid longitudinally through the bushing 30. A Dacron felt cuff 36 surrounds the outside of the bushing 30 and is used to assist in the implant of the bushing 30 into a body wall of the patient.

The apparatus 10 as stated above is for use in in situ radiotherapy of a patient. In particular, the apparatus 10 is useful for in situ radiotherapy of deep lying tumors, for example, within the abdominal cavity or the thoracic cavity of the patient. As is known from the prior art, certain cancers may be treated by implanting tubes through the tumor mass and periodically placing radioactive substances within the tubes. As described in the above cited copending applications, the radioactive substances are in the form of a wire having a radioisotope imbedded in a nominally nonradioactive material. The radioisotope is relatively localized and thus the wire may be extended into the guide tube with the isotope's being relatively well positioned with respect to the tumor. However, treating physicians recognize that the guide tubes must remain relatively immobile in the patient during the entire treatment therapy. In some cases it is desirable for the treatment to last as long as two to three weeks. In the past, it has proven impossible to implant a deep dwelling tumor with guide tubes since it has been impossible to find anchor points outside the body for such tumors. Recognizing this drawback, the apparatus 10 which includes a plurality of anchors 14 for attachment to healthy tissue within the body after the guide tubes 12 are drawn through the tumor has been developed. It is also important to seal the ends of the guide tubes to prevent the patient's being infected by any materials within the guide tubes.

Figure 3:
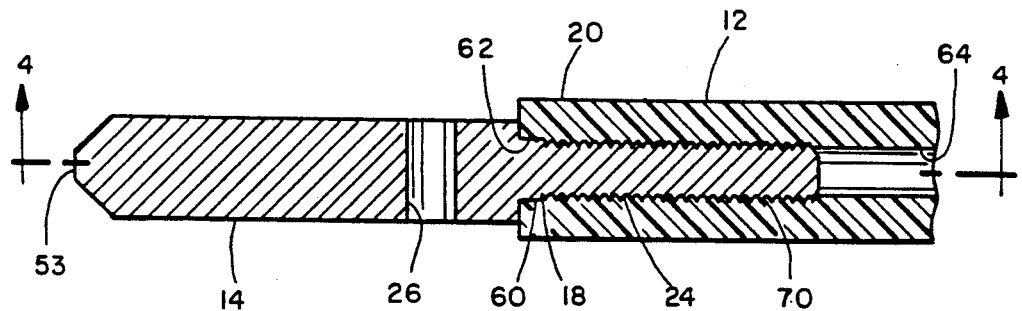
FIG. 3 is a section taken substantially along line 3—3 of FIG. 1 showing details of an anchor threadedly connected to one of the catheters.
Figure 4:
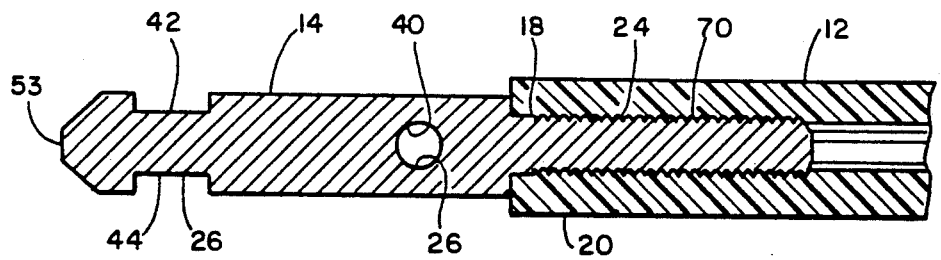
FIG. 4 is a section taken substantially along line of 4—4 of FIG. 3 showing further details of the anchor and the catheter.

As may best be seen in FIGS. 3 and 4, attachment means 26 includes an aperture or suture eye 40 formed integral with each of the anchors 14 and a slotted head portion comprising a first slot 42 and a second slot 44 also formed integral with the anchor 14. The apertures 40 are adapted to receive or have threaded through them a suture for suturing of the anchors 14 to healthy tissue. Typically a figure eight suture would be used. The slots 42 and 44 are adapted to be engaged by a vascular clip which would also engage healthy tissue and permanently or semi-permanently connect the anchor 14 to the healthy tissue. The slots 42, 44 and the aperture 40 are alternative attachment means; the surgeon may take his choice.

Of course, prior to the connection of the anchor it is necessary to introduce the flexible catheters 12 into the body. This is typically done during surgical procedures wherein the surgeon concludes that the tumor which has been examined or partially exposed is non-resectable Such tumors may be in the brain, the pancreas, the bowel and various portions of the thoracic and abdominal cavities. In order to implant the catheters 12 in the tumor, the surgeon typically uses a backbone stylet. He places it in one of the catheters 12 with a respective anchor 14 attached and drives the stylet through a tumor mass 50, as may best be seen in FIG. 5, to the other side and positions the anchor 14 in proximity to healthy tissue 52. It may be appreciated that a penetrant point 53 connected to the anchor 14 and preferably integral therewith aids in forcing the flexible catheter 12, stiffened by the stylet, through the tumor 50. A suture 54 may then be drawn through the aperture 40 and stitched into place in the healthy tissue 52 thereby anchoring the anchor 14 or permanently connecting it to the healthy tissue 52. It should be appreciated that other means for driving the catheters 12 through tumor mass 50 can also be employed. For example, apparatus can be affixed outside of catheter 12 to anchor 14 and used to drive the anchor 14 and the attached catheter 12 through the tumor.

If the surgeon does not wish to use sutures as an alternative he may clip a vascular clip to the healthy tissue and to the slots 42 and 44 connected to the anchor 14. In either case the anchor 14 is fixed with respect to the healthy tissue 52, thereby fixing the catheter 12 with respect to the tumor body 50.

It may be appreciated that the multiple catheters 12 may be flexed, although it is desirable from the standpoint of the surgical procedures to make sure that the radius of curvature of the guide tubes is kept large as to permit insertion of the radioactive source. The catheters 12 may be implanted in three dimensional patterns throughout the tumor 50 in conformity with well-known therapeutic regimens. Such regimens provide the maximum radiation flux within the tumor body 50 and lower radiation flux outside the tumor body 50.

Once the distal ends 20 of the catheters 12 have been so anchored it may be appreciated that because each catheter 12 is to remain in the body for a length of time, it is important that the catheter ends are sealed to prevent infection. The sealing means 18 consists of a collar 60 which is formed integrally with the anchor 14. The collar 60 receives the distal end 20 of the catheter 12 thereon and slightly expands an opening 62 in the distal end 20 to form a tight seal therewith to prevent the entry into the body of any materials or contaminants from within a bore 64 of the catheter 12. It may also be appreciated that each of the anchors 14 is connected removably to the distal end 20 of its respective catheter 12 by a thread 70 connected to the anchor 14, preferably formed integrally therewith. The thread 70 is the means for removably connecting the anchor to the distal end 20 of the catheter 12. That is, by turning the catheter 12, it is unscrewed from the anchor 14, permitting withdrawal of the catheter 12 from the body, leaving the anchor fixed in the body. This removable connection feature is important for reasons which will become apparent hereinafter. Although the thread 70 was employed as the removable connection, other releasable connecting means might also be employed by one skilled in the art.

Figure 6:
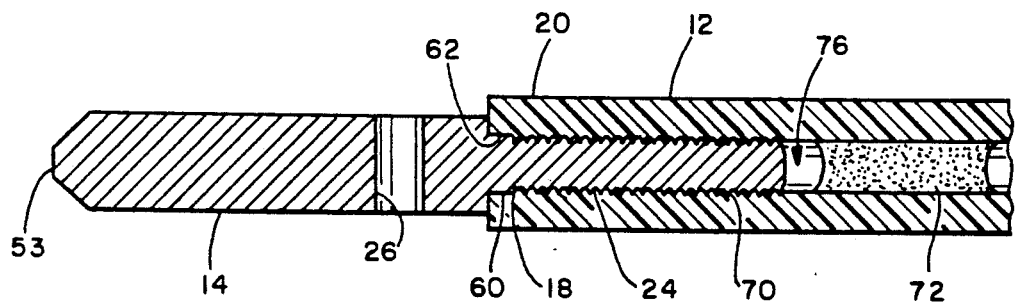
FIG. 6 is an alternative embodiment of FIG. 3 showing a catheter sealing adhesive.

When the anchor 14 is disconnected from the respective catheter 12, the distal end seal provided by the sealing means 18 no longer exists. In order to prevent contaminants from entering the body, a second seal (FIGS. 6 and 7) is provided at the distal end 20 of each catheter. FIG. 6 shows a second seal 72 formed of adhesive which is injected into the catheter 12 prior to the attachment of anchor 14 to the catheter. The adhesive should be injected farther into the catheter than the threaded end of the anchor 14 will reach, leaving a space 76 between the inserted anchor and the second seal 72. The adhesive used for the seal 72 should be medically inert and capable of bonding with catheter 12. When the catheter 12 and the anchor 14 are to be forced through tumor mass 50 using a stylet inside catheter 12, the adhesive should also be of sufficient hardness and the bond to catheter 12 sufficiently strong to resist penetration by the stylet. Alternatively, when the driving force is applied to anchor 14 outside of catheter 12, no penetration forces will be applied to second seal 72 and a softer adhesive may be desirable to provide greater flexibility of the catheter 12.

Figure 7:
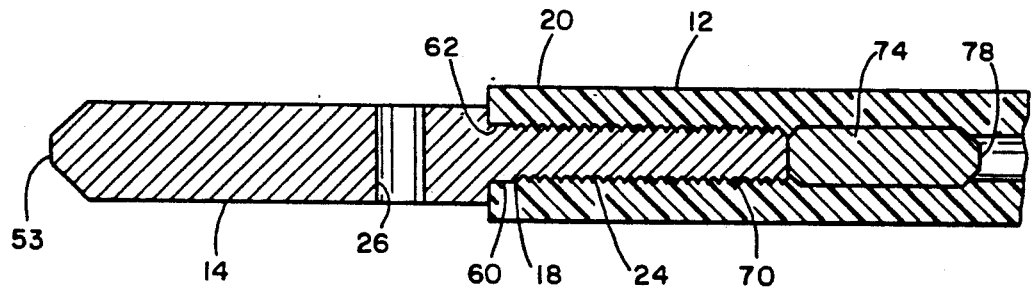
FIG. 7 is an alternative embodiment of FIG. 3 showing a solid cylindrical catheter sealing apparatus.

FIG. 7 shows an alternative embodiment to the second seal 72 of FIG. 6. The second seal in FIG. 7 is provided by a solid cylinder 74 as of stainless steel, having a diameter slightly larger than the inner diameter of bore 64. Preferably, one end of cylinder 74 is shaped as the frustum of a right circular cone having an end 78 of smaller diameter than the inner diameter of bore 64. During the assembly of catheter 12, the cylinder 72 may be driven into the distal end of catheter 12 a distance less than the length of the anchor connector 24. When the anchor 14 is completely screwed to the catheter 12, the anchor connector 24 will force the cylinder 74 into the catheter 12 and the cylinder 74 will abut the anchor connector 24. A second seal is provided by the arrangement, because the catheter will expand slightly and form a tight seal around the larger diameter cylinder 74. In the present embodiment, stainless steel has been used for cylinder 74. The cylinder 74 could be fabricated from other materials which are medically inert and of sufficient strength and hardness to permit a tight second seal with catheter 12 and to resist the penetrating forces applied by a surgical stylet inside the catheter.

It may also be appreciated that although the attachment of the anchors 14 to the healthy tissue 52 has been described herein as a permanent attachment, the attachment is permanent in the sense that during the period for which the catheter 12 is to remain in the body and for a period thereafter the anchors 14 will remain implanted. This may be for the life of the patient; however, should the treating physician so desire, he or she is always free to perform another surgical procedure on the patient and remove the vascular clips or sutures 54 thereby releasing the anchors 14 from the healthy tissue 52. Because such a procedure will involve risk to the patient who has already been weakened by the malignancy, a primary advantage of this invention lies in the fact that the anchors 14 may be released remotely from the catheters 12 to which they are connected after the radiotherapy regimen is completed. The anchors 14 may be removed, if at all, after the patient has recovered.

Returning to the problems faced by the physician as he implants the apparatus 10, the bushing 30 is positioned so that approximately one quarter inch to one inch will be free to extend outside a skin surface 80 of the patient to be treated. The Dacron felt cuff is positioned so that it is slightly below the level of the skin 80 of the patient and in proximity with the subcutaneous fat layer and the dermis. The surgeon attaches the bushing 30 to the patient's body by looping a suture around the bushing 30 and attaching it to the underlying tissue layers. The surgeon may also wrap a suture around the bushing 30 on the opposite side of the Dacron felt cuff 36 to secure the proximal side of the bushing 30 to the dermis of the patient. The surgeon then trims the catheters 12 to a length of about twelve centimeters from the proximal end of the bushing 30. At this point, because the surgical procedure is being completed and radiotherapy will not be started until the patient recovers from his or her surgery typically the proximal portions of the catheters 12 are coiled and a skin flap is pulled over the bushing 30 and the proximal ends of the catheters 12, thereby completely enclosing the apparatus 10 within the patient's body while recovery takes place.

Figure 8:
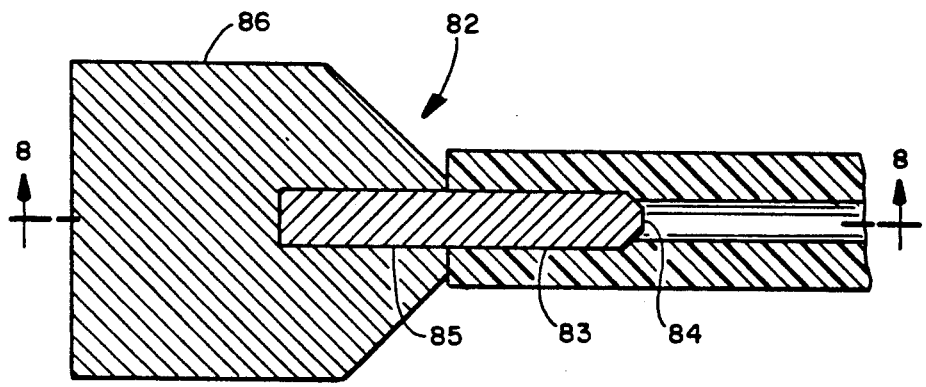
FIG. 8 is a section taken substantially along line 8—8 of FIG. 1 showing a catheter with a proximal catheter end sealing apparatus inserted therein.

Before enclosing the catheters 12 in the body, their proximal ends 22 are sealed. FIG. 8 shows an embodiment of a catheter sealing apparatus 82 for use with the proximal ends of a catheter 12. The catheter sealing apparatus 82 is comprised of a manipulating portion or handle 86 and a catheter sealing portion 83. In the present embodiment, the sealing portion 83 is a stainless steel cylinder having a diameter slightly in excess of the inner diameter of the catheter 12. The end 84 of the sealing portion 83 is tapered so that it can be readily inserted into the catheter 12. The sealing portion 83 is affixed by an adhesive to a cylindrical recess 85 in the handle 86. The handle 86 of the present embodiment is made of polytetrafluoroethylene and has a diameter of approximately twice the outer diameter of catheter 12. The size and shape of handle 86 should be chosen to be large enough for easy manipulation while small enough to be enclosed within the patient's body awaiting recovery from surgery. Alternatively, machine screws may be screwed into the proximal ends to seal the ends.

Once the physician elects to begin the radiotherapy treatment, the catheters 12 and the bushing 30 will be freed partially from the skin 80 so that the bushing now protrudes a short distance outside the skin surface 80 as may be seen in FIG. 5. The seals are removed from the proximal ends 22, which are then connected to a radioisotope source afterloader such as that described in the aforementioned application of Spako et. al., via quick-connects of the type normally used in the medical art. The afterloader then feeds source wires down each of the catheters 12. Because the catheters 12 are immobilized with respect to the tumor 50 by the anchors 14, the treating physician may easily select the axial points within the catheters 12 at which he wishes the iridium 192 in the source wire to be positioned during treatment.

Because only a single opening is made in the patient's body, and the Dacron felt cuff 36 allows inward growth of tissue into contact with the bushing 30 to take place, the risk of infection is drastically reduced. This will allow the catheters 12 to remain in in place for several weeks during which time a sequence of treatments may be carried out on the patient exposing the patient to relatively high doses of radiation in the tumor region several times, a regimen that provides better therapeutic results.

The prior art methods were more prone to infection, the catheters could be implanted only for shorter periods of time, for instance, two to three days. Although the patient received the same total dosage of radiation, not all the cancer cells could be killed. This resulted from the fact that the sources were left in the patient for the entire two or three day period. The present invention allows the patient to be exposed to radiation for brief intervals. Multiple exposures are employed which are spread over several weeks. The extended treatment destroys more of the tumor.

Once the physician has completed the radiotherapy treatment after two or three weeks, the bushing 30, Dacron cuff 36 and the catheters 12 may be withdrawn from the patient's body. The surgeon dissects away the tissue from the Dacron cuff 36 under local anesthetic and using aseptic procedures using a buttonhole incision. The sutures securing the bushing 30 are removed and the bushing 30 is elevated away from the tissue. The catheters 12 are then each clamped with a hemostat or again sealed by the sealing apparatus 82 of FIG. 8 and cut away from the bushing 30. At that point, the guide tubes 12 are each rotated causing the distal ends to be unthreaded from the threads 70 connected to the anchors 14. The catheters 12 may then be withdrawn from the body while the anchors are left in and the patient is protected from contamination by the second seal 72 or 74 at the catheter distal end. The patient has the benefit of long-term radiotherapy on deep-lying tumor without many of the surgical risks.

While there has been illustrated and described a particular embodiment of the present invention, it would be appreciated that numerous changes and modifications may be made within the true scope of the present invention.

What is claimed is:

1. Apparatus for in situ radiotherapy of a patient, comprising:
   a flexible guide tube having a proximal end for receiving a radioisotope and a distal end for positioning the guide tube within a patient to be treated;
   sealing means comprising a plug filling a portion of said guide tube for sealing the distal end of the guide tube; and
   an anchor including anchor connector means for to the flexible guide releasably connecting the anchor tube, and patient connection means for connecting the anchor permanently to the patient.

2. The apparatus according to claim 1, wherein said sealing means comprises a plug of adhesive filling a portion of said guide tube.

3. The apparatus according to claim 1, wherein said guide tube is deformable and said sealing means comprises a cylindrical plug larger than the undeformed interior of said guide tube distal end such that said guide tube forms a seal with said cylindrical plug.

4. Apparatus for in situ radiotherapy of a patient, comprising:
   a flexible guide tube having a proximal end for receiving a radioisotope and a distal end for positioning the guide tube within a patient to be treated;
   an anchor, including first sealing means integral with said anchor, for sealing the distal end of the guide tube, anchor connector means for releasably connecting the anchor to the flexible guide tube, and patient connection means for connecting the anchor permanently to the patient; and
   second sealing means in said guide tube for sealing the distal end of the guide tube at a point closer to the proximal end of said guide tube than said first sealing means.

5. The apparatus according to claim 4, wherein the flexible guide tube comprises a catheter.

6. The apparatus according to claim 4, wherein said anchor connector means extends a first distance into said guide tube distal end and said second sealing means comprises a plug of adhesive filling a portion of said guide tube at a second distance from said distal end, said second distance being greater than said first distance.

7. The apparatus according to claim 6, wherein said anchor connector means comprises a screw thread which engages the guide tube.

8. The apparatus according to claim 4, wherein said guide tube is deformable and said second sealing means comprises a cylindrical plug larger than the undeformed interior of said guide tube distal end such that said guide tube forms a seal with said cylindrical plug.

9. The apparatus according to claim 8, wherein said cylindrical plug is formed of stainless steel.

10. The apparatus according to claim 8, wherein said anchor connector means extends into said guide tube distal end and abuts said cylindrical plug.

11. The apparatus according to claim 4, comprising removable means for sealing the proximal end of said guide tube.

12. Apparatus for in situ radiotherapy of a patient, comprising:

flexible guide tube having a proximal end for receiving a radioisotope and a distal end for positioning the guide tube within a patient to be treated;

an anchor;

distal end sealing means for sealing the distal end of the guide tube;

anchor connector means for releasably connecting the anchor to the flexible guide tube;

patient connection means connected to the anchor for connecting the anchor permanently to the patient; and proximal end sealing means for sealing said proximal guide tube end when said proximal guide tube end is not receiving said radioisotope.

13. The apparatus according to claim 12, wherein said proximal end sealing means comprises a cylindrical plug for insertion into said proximal guide tube end and a handle connected to said cylindrical plug for the manual insertion and removal of said cylindrical plug with said guide tube.

14. The apparatus according to claim 13 wherein said guide tube is deformable and said cylindrical plug is larger than the undeformed interior at said guide tube proximal end.

* * * * *

UNITED STATES PATENT AND TRADEMARK OFFICE
CERTIFICATE OF CORRECTION

PATENT NO. : 5,183,455
DATED : February 2, 1993
INVENTOR(S) : Michael H. Hayman et al.

It is certified that error appears in the above-identified patent and that said Letters Patent is hereby corrected as shown below:

At column 1, lines 14-15, after "1988" insert --Spako,--; and after "et al.", delete "now U.S. Patent No. 4,976,680, issued December 11, 1990" and insert --; and--.

At column 1, line 26, change "non-respectable" to --non-resectable--.

At column 3, line 26, after "line" delete "of".

At column 3, line 46, after "catheters" change "of" to --or--.

At column 3, line 50, after "18" change "if" to --is--.

At column 7, line 38, delete "in" (second occurrence).

At column 8, line 20 (claim 1), after "guide" (line 21) delete "releasably connecting the anchor," and after "for" (line 20) insert --releasably connecting the anchor--.

Signed and Sealed this

Twenty-second Day of February, 1994

*Attest:*

BRUCE LEHMAN

*Attesting Officer*     *Commissioner of Patents and Trademarks*